United States Patent
Gilboa

(10) Patent No.: US 9,202,387 B2
(45) Date of Patent: Dec. 1, 2015

(54) METHODS FOR PLANNING AND PERFORMING PERCUTANEOUS NEEDLE PROCEDURES

(75) Inventor: Pinhas Gilboa, Haifa (IL)

(73) Assignee: STRYKER LEIBINGER GMBH & CO. KG, Freiburg (DE)

( * ) Notice: Subject to any disclaimer, the term of this patent is extended or adjusted under 35 U.S.C. 154(b) by 321 days.

(21) Appl. No.: 13/498,142

(22) PCT Filed: Nov. 11, 2010

(86) PCT No.: PCT/IB2010/055130
§ 371 (c)(1),
(2), (4) Date: Mar. 25, 2012

(87) PCT Pub. No.: WO2011/058516
PCT Pub. Date: May 19, 2011

(65) Prior Publication Data
US 2012/0215096 A1     Aug. 23, 2012

Related U.S. Application Data

(60) Provisional application No. 61/260,026, filed on Nov. 11, 2009, provisional application No. 61/300,453, filed on Feb. 2, 2010, provisional application No. 61/313,747, filed on Mar. 14, 2010.

(51) Int. Cl.
*A61B 6/02* (2006.01)
*A61B 6/00* (2006.01)
*G09B 23/28* (2006.01)
*A61B 19/00* (2006.01)

(52) U.S. Cl.
CPC ............... *G09B 23/28* (2013.01); *A61B 19/52* (2013.01); *A61B 19/5244* (2013.01); *A61B 19/54* (2013.01); *A61B 2019/5251* (2013.01)

(58) Field of Classification Search
CPC ............... A61B 19/52; A61B 19/5244; A61B 2019/5251; A61B 19/54; G09B 23/28
USPC ............... 600/407, 411, 414, 424, 426
See application file for complete search history.

(56) References Cited

U.S. PATENT DOCUMENTS 6,478,793 B1    11/2002   Cosman et al.
2001/0033682 A1*   10/2001   Robar et al. ............. 382/132

(Continued)

FOREIGN PATENT DOCUMENTS

IL    WO2007113815    10/2007
IL    WO2008107874    9/2008

*Primary Examiner* — Baisakhi Roy
(74) *Attorney, Agent, or Firm* — Howard & Howard Attorneys PLLC

(57) ABSTRACT

A system and method for planning volumetric treatment by percutaneous needle procedures obtains a volumetric image data set of a subject including an identifiable region requiring treatment. An effective treatment volume is defined relative to the needle position for at least one needle carrying a treatment applicator. One or more proposed inserted needle position is defined such that a effective treatment volume corresponding to the one or more proposed inserted needle position provides coverage of the region requiring treatment. The effective treatment volume for one or more needles can then be visualized in the context of slices of 3D image data. One or more entry point and corresponding virtual target are then defined relative to a frame of reference of the volumetric image data set for use in navigation of the at least one needle to the corresponding proposed inserted needle position.

11 Claims, 14 Drawing Sheets

(56) References Cited

U.S. PATENT DOCUMENTS

| | | | |
|---|---|---|---|
| 2002/0070365 A1* | 6/2002 | Karellas | 250/581 |
| 2003/0130576 A1 | 7/2003 | Seeley | |
| 2005/0148854 A1* | 7/2005 | Ito et al. | 600/407 |
| 2008/0181358 A1* | 7/2008 | Van Kampen et al. | 378/8 |
| 2009/0039268 A1* | 2/2009 | Peter et al. | 250/363.04 |
| 2009/0221908 A1 | 9/2009 | Glossop | |
| 2010/0137707 A1* | 6/2010 | Hunter et al. | 600/424 |
| 2012/0179026 A1* | 7/2012 | Simon et al. | 600/411 |

\* cited by examiner

METHODS FOR PLANNING AND PERFORMING PERCUTANEOUS NEEDLE PROCEDURES

FIELD AND BACKGROUND OF THE INVENTION

The present invention relates to percutaneous needle procedures and, in particular, it concerns systems and methods for planning and performing such procedures.

It is known to perform a range of procedures employing a needle inserted through the skin (i.e., percutaneously) to reach a site within the body. All such procedures are referred to herein as "percutaneous needle procedures". These procedures may be therapeutic or diagnostic, and may employ needles carrying a range of tools or payloads.

Interventional Radiology (IR) employs one or more of a number of imaging modalities to facilitate planning and/or navigation of a needle for performing percutaneous needle procedures. Of particular significance during the planning stages are volumetric imaging techniques, such as computed tomography (CT) and magnetic resonance imaging (MRI), which provide a three dimensional volume-imaging data set in which each value is associated with a "voxel" (volume pixel) of the body. These images can be used by a practitioner to identify the target location within the body and choose a point of entry which will allow him or her to reach the target location with minimum damage to body organs, and without being blocked by mechanical obstructions such as bones.

There are various Computer-Guiding systems known in the art, which may be used to guide a needle to intra-body target based on pre-acquired volumetric images, such as CT images. One preferred example is described in WO 2007/113815 to Gilboa, which is fully incorporated herein by reference. In such systems, a volumetric-imaging data set is imported in DICOM format to the system and displayed on a screen. By registering the image space to the physical space, and by tracking a needle in this space, a practitioner may aim and guide a needle towards a target displayed on the screen.

A method and system for planning the route of the needle to an intra-body target is described in WO 20081107874, entitled "A Method and Device for Planning Image-Guided Needle Procedures" to Gilboa, which is fully incorporated herein by reference.

In some of the procedures, the target is well identified by its anatomical shape and the tip of the needle needs to be directed into the target. An example of such procedure is Fine Needle Aspiration Biopsy (FNA) in which a long thin needle is directed into a lesion to extract sample cells. For such procedures, the combination of the aforementioned planning system together with the aforementioned computer-aided guiding during performance of the procedure are typically highly effective.

There are other types of procedures, however, in which the medical action takes place within an effective treatment volume defined relative to the needle position, and typically at an offset displacement from the needle tip. In such cases, the optimum location of the needle does not coincide with an identifiable anatomical feature, so in practice the needle should be guided to an arbitrary spot in space. An example of such a procedure is the thermal ablation of a tumor in which the ablation zone should envelop the tumor, so the needle should be placed at an exact spot within the lesion which cannot always be easily estimated just by looking at the cross section of the lesion. Even more complex is the ablation of a tumor using two or more needles (or a single needle placed sequentially at a plurality of locations) in which case the needles may need to be placed adjacent to the tumor rather than at its center.

There is a benefit to use the planning described in WO 2008/107874 combined with the guidance described in WO 2007/113815. However, each requires its own separate 3D image. In addition, when the clinical procedure requires guidance of more than one needle concurrently, each needle requires its own sticker and the number of scans required is multiplied by the number of needles to be used.

Hence, it would be desirable to provide a new device and method to combine the 3D scanning required for WO 2008/107874 with the data required to use WO 2007/113815 when guiding one or more needles while requiring only a single scan. This would save time and harmful radiation in the case of using ionizing radiation.

There is therefore a need for systems and methods for planning and performing percutaneous needle procedures which will facilitate correct positioning of one or more needles for volumetric treatment in cases where the optimal locations of the needles do not coincide with identifiable anatomical features. It would also be advantageous to provide systems and methods for planning and performing percutaneous needle procedures in which the overall number of repeat scans of the body is kept to a minimum, thereby reducing the required radiation exposure of the body.

SUMMARY OF THE INVENTION

The present invention relates to percutaneous needle procedures and, in particular, it concerns systems and methods for planning and performing such procedures.

According to an embodiment of the present invention there is provided, a method for planning volumetric treatment comprising the steps of (a) obtaining a volumetric image data set of a subject including an identifiable region requiring treatment; (b) defining an effective treatment volume for at least one needle carrying a treatment applicator, the effective treatment volume being defined relative to the position of the needle; (c) defining one or more proposed inserted needle position such that a effective treatment volume corresponding to the one or more proposed inserted needle position provides coverage of the region requiring treatment; and (d) defining relative to a frame of reference of the volumetric image data set one or more entry point and corresponding virtual target for use in navigation of the at least one needle to the corresponding proposed inserted needle position.

According to a further feature of an embodiment of the present invention, a graphic representation of the extent of the effective treatment volume is displayed in the context of a plurality of images representing data from the volumetric image data set so as to allow verification by a user that the effective treatment volume corresponding to the one or more proposed inserted needle position provides coverage of the region requiring treatment.

According to a further feature of an embodiment of the present invention, the graphic representation of the extent of the effective treatment volume is provided at least in part by changing a visual property of a region of the images lying within the effective treatment volume.

According to a further feature of an embodiment of the present invention, the one or more proposed inserted needle position is defined by a user by adjustment of the proposed inserted needle positions in a graphic user interface including: (a) a display of an image representing data from a volumetric image data set so as to render visible a region requiring treatment; and (b) a graphic representation of the effective treatment volume for the needle, the graphic representation being shown in the context of the displayed image for a proposed inserted needle position.

According to a further feature of an embodiment of the present invention, the one or more proposed inserted needle position is defined by an automated process including: (a) delineating limits of the region requiring treatment in three dimensions; and (b) optimizing positioning of the effective treatment volume of the one or more needle according to a predefined set of criteria.

According to a further feature of an embodiment of the present invention, the effective treatment volume is delineated by a geometrical surface centered at an offset from a tip of the at least one needle, and wherein the virtual target corresponds to a location to which the tip of the needle should be brought.

According to a further feature of an embodiment of the present invention, the region requiring treatment has at least one dimension greater than the effective treatment volume, and wherein entry points and corresponding virtual targets are defined for at least two proposed inserted needle positions such that the combined effective treatment volume for the at least two proposed inserted needle positions provides coverage of the region requiring treatment.

According to a further feature of an embodiment of the present invention, insertion paths extending from the entry points to the corresponding virtual targets are non-parallel.

There is also provided according to an embodiment of the present invention, a method for determining the position of a set of optical navigation markers on the surface of a body, the method comprising the steps of: (a) deploying on the surface of the body a set of at least four registration fiducial markers; (b) deploying on the surface of the body a set of at least four navigation fiducial markers, the set of navigation fiducial markers being distinct from the set of registration fiducial markers; (c) employing an imaging system including at least one two-dimensional imaging device to obtain at least two images taken along different viewing directions, each of the at least two images including both the registration fiducial markers and the navigation fiducial markers; (d) deriving from positions of the set of registration fiducial markers in each of the images a corresponding position and orientation of the imaging system relative to the registration markers; and (e) deriving from positions of the set of navigation fiducial markers within the at least two images a position of the navigation fiducial markers in a frame of reference associated with the registration fiducial markers.

According to a further feature of an embodiment of the present invention, the at least one imaging device is a video camera.

According to a further feature of an embodiment of the present invention, there are also provided the steps of: (a) obtaining a volumetric image of at least part of the body including a target, subsequent to deploying of the registration fiducial markers and prior to deploying of the navigation fiducial markers; (b) deriving locations of the registration fiducial markers relative to the volumetric image; and (c) deriving a position of the target relative to the navigation fiducial markers.

According to a further feature of an embodiment of the present invention, the registration fiducial markers include markers readily discernable in the volumetric image, thereby facilitating the deriving locations of the registration fiducial markers.

According to a further feature of an embodiment of the present invention, the deriving locations of the registration fiducial markers includes sampling optical images of the registration fiducial markers from two optical image sensors deployed in known spatial relation to a volumetric imaging system employed to obtain the volumetric image.

According to a further feature of an embodiment of the present invention, there are also provided the steps of: (a) providing a tool having a camera mounted in fixed relation thereto, and deployed so as to obtain images including the navigation fiducial markers; and (b) providing a navigation display indicative of a relative position between the tool and the target derived from the position of the navigation fiducial markers within the images.

There is also provided according to an embodiment of the present invention, a system for achieving registration between an intra-body target and a set of one or more optical fiducial markers, the system comprising: (a) a volume imaging device for generating images of the body; (b) two optical image sensors deployed in known spatial relation to the volume imaging device; and (c) a processing system associated with the volume imaging device and the optical image sensors, the processing system configured to: (i) process images from the two optical image sensors to derive the location of at least one optical fiducial marker relative to the optical image sensors, and (ii) define the location of the at least one optical fiducial markers within a coordinate system of the volume imaging device.

There is also provided according to an embodiment of the present invention, a method for achieving registration between an intra-body target and a set of one or more optical fiducial markers, the method comprising the steps of: (a) providing an imaging system comprising: (i) a volume imaging device for generating images of the body, and (ii) two optical image sensors deployed in known spatial relation to the volume imaging device; (b) processing images from the two optical image sensors to derive the location of at least one optical fiducial marker relative to the optical image sensors; and (e) defining the location of the optical fiducial marker within a coordinate system of the volume imaging device.

According to a further feature of an embodiment of the present invention, the volume imaging system is a C-a in fluoroscope, and wherein the two optical image sensors are mounted on the C-arm.

According to a further feature of an embodiment of the present invention, there are also provided the steps of: (a) obtaining images using the C-arm fluoroscope deployed in at least two different angular positions; (b) identifying an intra-body target in both of the fluoroscope images; and (c) deriving a spatial relationship between the intra-body target and the at least one optical fiducial marker.

According to a further feature of an embodiment of the present invention, the volume imaging system is a volumetric imaging system having a gantry, and wherein the two optical image sensors are mounted on the gantry.

BRIEF DESCRIPTION OF THE DRAWINGS

The invention is herein described, by way of example only, with reference to the accompanying drawings, wherein.

DESCRIPTION OF THE PREFERRED EMBODIMENTS

Figure 1:
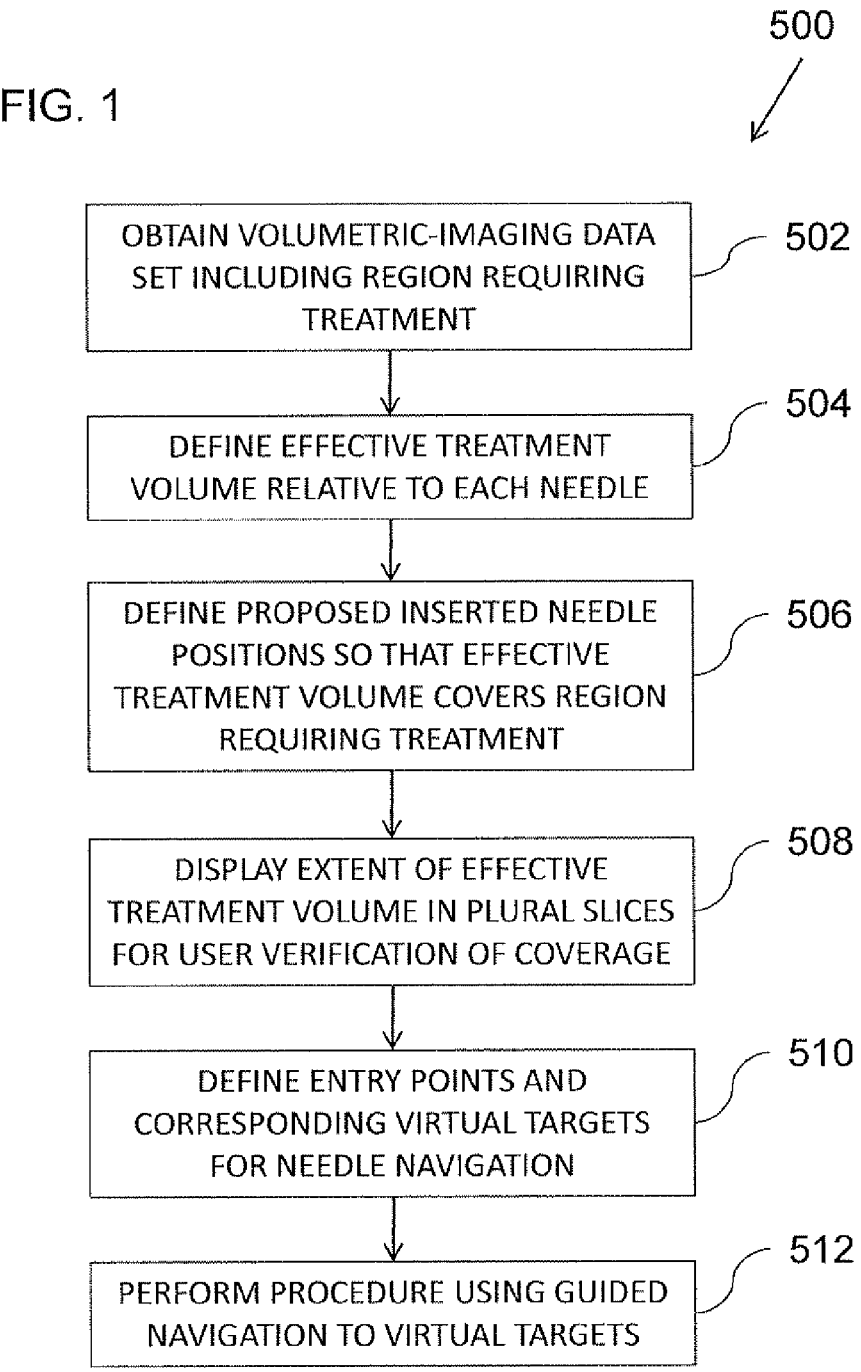
FIG. 1 is a flow diagram of a method according to an embodiment of the present invention for planning volumetric treatment by a percutaneous needle procedure.

The present invention relates to percutaneous needle procedures and, in particular, it concerns systems and methods for planning and performing such procedures.

The principles and operation of systems and methods according to the present invention may be better understood with reference to the drawings and the accompanying description.

By way of introduction, a number of different aspects of the present invention will be presented herein, each of which is believed to be of patentable significance in its own right, but which may be used together in synergy to particular advantage. Thus a first aspect of the invention, described herein through one or more non-limiting embodiments with reference to FIGS. 1-15, relates to a system and method for planning volumetric treatment by a percutaneous needle procedure. A second aspect of the invention, described herein through one or more non-limiting embodiments with reference to FIGS. 16-21, relates to a system and method for achieving registration of optical markers to intra-body features, and may be used, for example, to advantage when performing the procedure planned according to the first aspect of the invention.

Definitions

Before addressing examples of the present invention in detail, it will be helpful to define certain terminology as used herein in the description and claims. Firstly, reference is made herein to various types of imaging systems. For the purpose of this document, a distinction will be made between "volume images" in which the image data is indicative of the properties of tissue within the body and "optical images" in which the image relates only to the outer surface of the body. According to this subdivision, fluoroscopy belongs to the class of "volume imaging" techniques.

A distinction will also be made between three dimensional (3D) images, also referred to herein as "volumetric images", in which each image data value relates to a volume unit or "voxel" of the body, and two dimensional (2D) images which are made up of pixel values in a 2D grid. According to this subdivision, fluoroscopy, which generates a 2D projection of the internal volume of the body belongs to the class of 2D imaging techniques.

The term "treatment applicator" is used herein to refer to any applicator or tool which acts on a volume of tissue around the needle to achieve a medically relevant effect. Examples include, but are not limited to, electrodes or antennae for delivering electromagnetic energy of any suitable frequency, cryoablation applicators, and mechanical tools.

The term "virtual target" is used to refer to a target location, typically defined relative to 3D image coordinates, which defines a desired location to which the tip of a needle should be brought for performing a procedure. The target is referred to herein as a "virtual" target in the sense that it does not typically correspond to any readily identifiable anatomical feature, but is rather chosen to achieve a desired overall effect. Thus, according to the circumstances, the virtual target for a given needle may fall off-center relative to a region to be treated, or may even lie outside the region to be treated, as will be discussed further below.

Volumetric Treatment Planning

Referring now to the drawings, FIG. 1 illustrates a method, generally designated 500, according to an embodiment of the first aspect of the present invention, for planning volumetric treatment via a percutaneous needle procedure. Method 500 includes obtaining a volumetric image data set of a subject including an identifiable region requiring treatment (step 502). An effective treatment volume is defined for at least one needle carrying a treatment applicator (step 504). The effective treatment volume is defined relative to the position of the needle, typically corresponding to a three-dimensional geometrical surface, such as an ellipsoid, centered at an offset from a tip of the at least one needle. For example, in the case of a needle carrying an RF ablation electrode, the effective treatment volume is typically an ellipsoid centered at or near the midpoint of the electrode. The geometrical properties of the effective treatment volume are generally provided by the tool manufacturer, and may have a range of values according to the operating parameters to be used. For the purpose of step 504, the effective treatment volume may be defined automatically, for example, in response to user selection of the type of needle and/or operating parameters to be used or, in other implementations, may be defined by the user.

One or more proposed inserted needle position are then defined such that a effective treatment volume corresponding to the one or more proposed inserted needle position provides coverage of the region requiring treatment (step 506). This process may be performed "manually" (i.e., by manipulation by the user via a graphic user interface), as will be described below in more detail with reference to FIG. 2, or in an automated or semi-automated manner, as will be described below in more detail with reference to FIG. 3. Optionally, at step 508, the overall extent of the effective treatment volume is displayed in a plurality of slices of the 3D image so as to allow user verification that the entire region requiring treatment has been effectively covered by the planned treatment volumes. This verification step is particularly important in the case of a fully automated implementation of step 506. The final planned inserted needle positions are then translated into corresponding entry points and virtual target points (step 510). Since each needle insertion path is assumed to be a straight line extending from the entry point towards the virtual target point and stopping when the needle tip reaches the virtual target point, these two points fully specify the planned path of insertion for each needle. This data is then used for navigation assistance, by any suitable guidance technology, during performance of the percutaneous needle procedure (step 512), which does not constitute part of the planning method.

Figure 2:
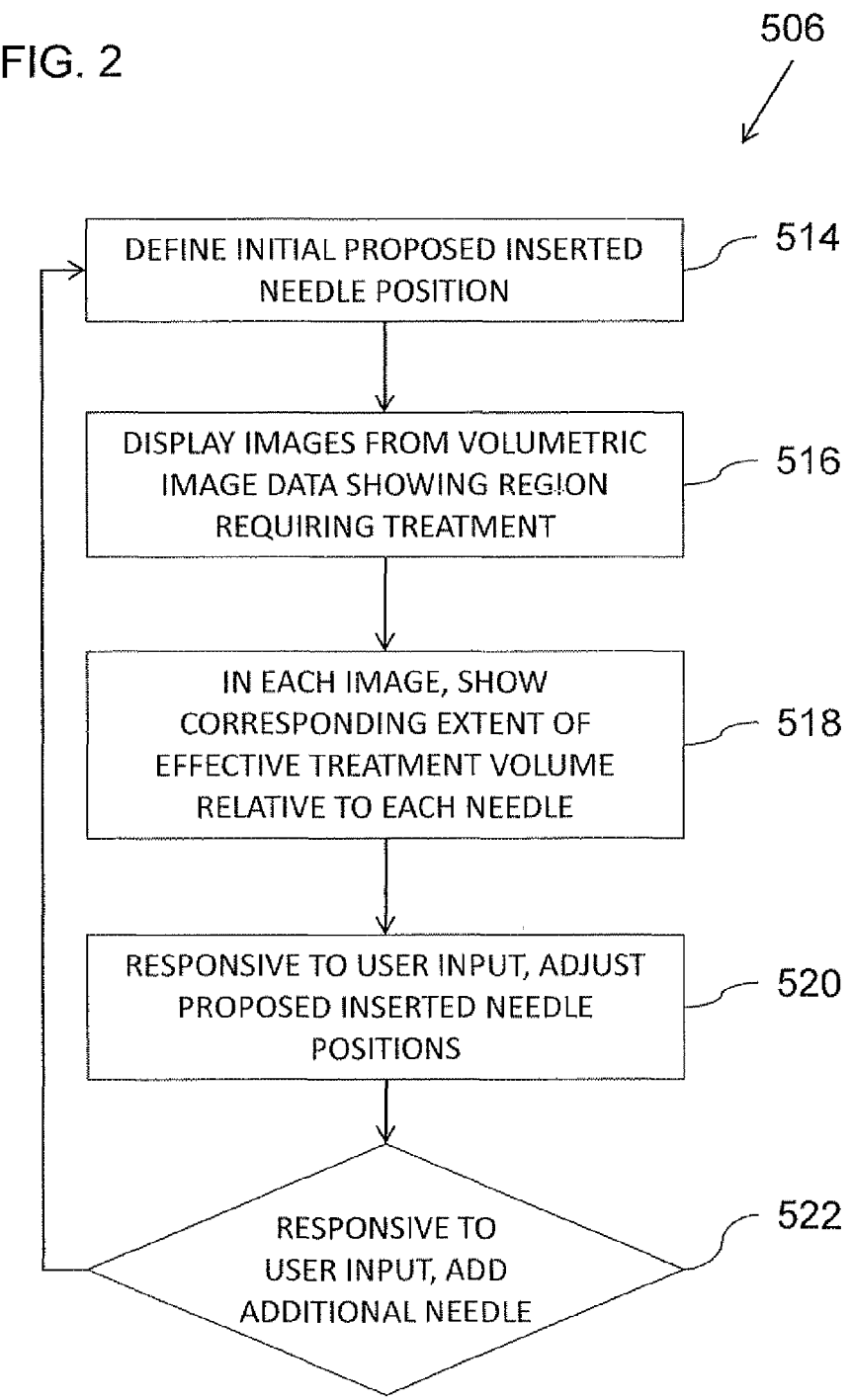
FIG. 2 is a more detailed flow diagram of block 506 from FIG. 1 according to a user-operated implementation of the method.

As mentioned, step 506 may be implemented in a number of ways. By way of example, FIG. 2 illustrates an implementation of step 506 in which the proposed inserted needle positions are defined by a user by adjustment of the proposed inserted needle positions in a graphic user interface. Specifically, as shown in FIG. 2, an initial approximation for an inserted needle position is first defined (step 514), typically based on approximate designation by the user of the target region and an insertion point. The system then generates images representing data from the volumetric image data set so as to render visible a region requiring treatment (step 516) and, in each image, shows a graphic representation of the effective treatment volume for the needle according to the proposed inserted needle position as it would intersect with the slice plane of the current image (step 518). The system then receives input from the user so as to allow the user to adjust the proposed inserted needle position(s), and thereby the coverage of the 3D region to be treated. Thus, the user can preferably scroll through a sequence of slices of the 3D image data and review a display of the intersection of the total effective treatment volume with each slice in turn, thereby seeing clearly whether the currently planned needle insertion positions give sufficient coverage of the 3D region to be treated, and making adjustment where needed. If the user sees that the number of needles employed in the current plan is insufficient to achieve full coverage, he or she can choose to add an additional needle (step 522) and repeat the positioning process for the additional needle as described above.

When the planned needle positions are adjusted, the user must also verify that the insertion path satisfies the other requirements of avoiding hard obstacles and delicate internal organs. Potential problems of this sort are typically resolved by adjusting the entry point for each needle. This may be done as part of the adjustment process of step 520, or as a separate subsequent step (not shown).

According to one preferred option for display in step 518 and/or in step 508 of FIG. 1, the extent of the effective treatment volume is visualized at least in part by changing a visual property of a region of the images lying within the effective treatment volume. For example, regions of a lesion lying within the effective treatment volume of needles already positioned may be rendered transparent, thereby clearly and intuitively indicating which parts of the lesion still lie outside the treatment envelope of the currently planned needle insertion positions.

Figure 3:
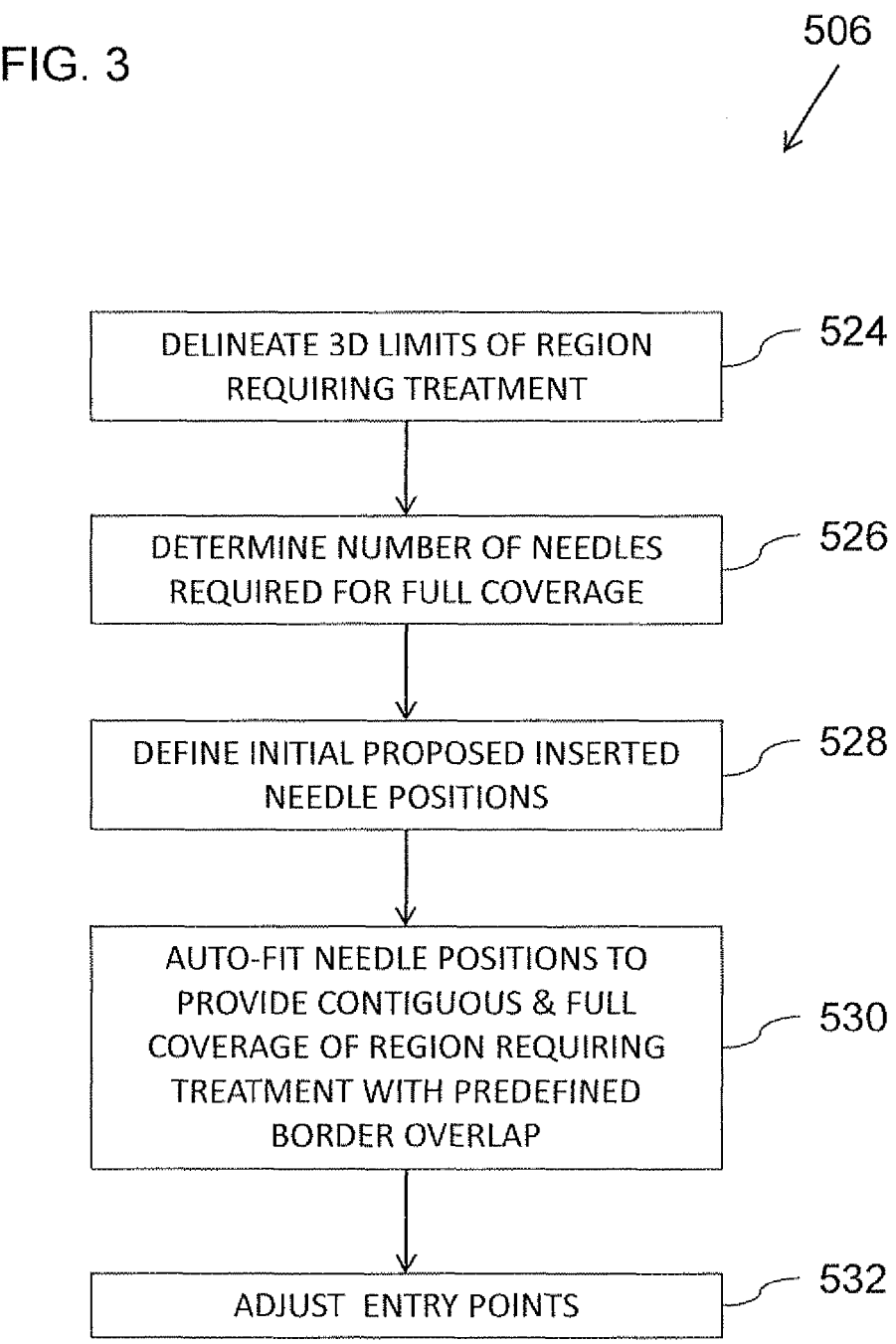
FIG. 3 is a more detailed flow diagram of block 506 from FIG. 1 according to an at least semi-automated implementation of the method.

Turning now to FIG. 3, this illustrates an alternative implementation of step 506 as an automated, or at least semi-automated, process. The process begins by delineating the limits of the region requiring treatment in three dimensions (step 524). This may be performed by receiving manually input boundary points selected by a user, automatically according to criteria applied to the image data directly, or by any other suitable technique. In the example illustrated here, the automated system then determines the number of needles required to achieve full coverage (step 526), calculates an initial proposed deployment for each needle (step 528) and performs an auto-fit optimization to ensure contiguous and full coverage of the region requiring treatment, preferably with a predefined margin of border overlap (step 530). It should be noted that the subdivision of this process into steps 526-530 is somewhat arbitrary, for the sake of clarity of presentation. In fact, for an automated process, it may be advantageous to combine these functions into a single process in which parameters of number of needles and an optimized position of each needle are solved in parallel, either by direct calculation or by iterative techniques. Alternatively, the automated process may parallel the example of a manual process presented above in which the positioning of individual needles is successively determined, and the next needle position is determined according to the parameters of the remaining portion of the region requiring treatment lying outside the treatment volume of the already-planned needles.

Finally, as before, the entry points of the needles may need to be adjusted to ensure that the insertion paths do not impinge on any hard obstructions or delicate internal organs (step 532). This adjustment is typically performed manually via a graphic user interface.

Parenthetically, it should be noted that a multi needle procedure planned according to this aspect of the present invention may frequently require insertion of needles along non-parallel paths, particularly in regions of the body such as the lungs and upper liver in which ribs may obstruct access to some virtual target points. This aspect of the present invention may be used to advantage with substantially any guidance technique which provides a required degree of accuracy. However, it is believed that the second aspect of the invention exemplified below with reference to FIGS. 16-21 provides particular synergy for reliable navigation of multiple non-parallel needles from different entry points to specific virtual targets within the body, as will become clearer from the description below.

Figure 4:
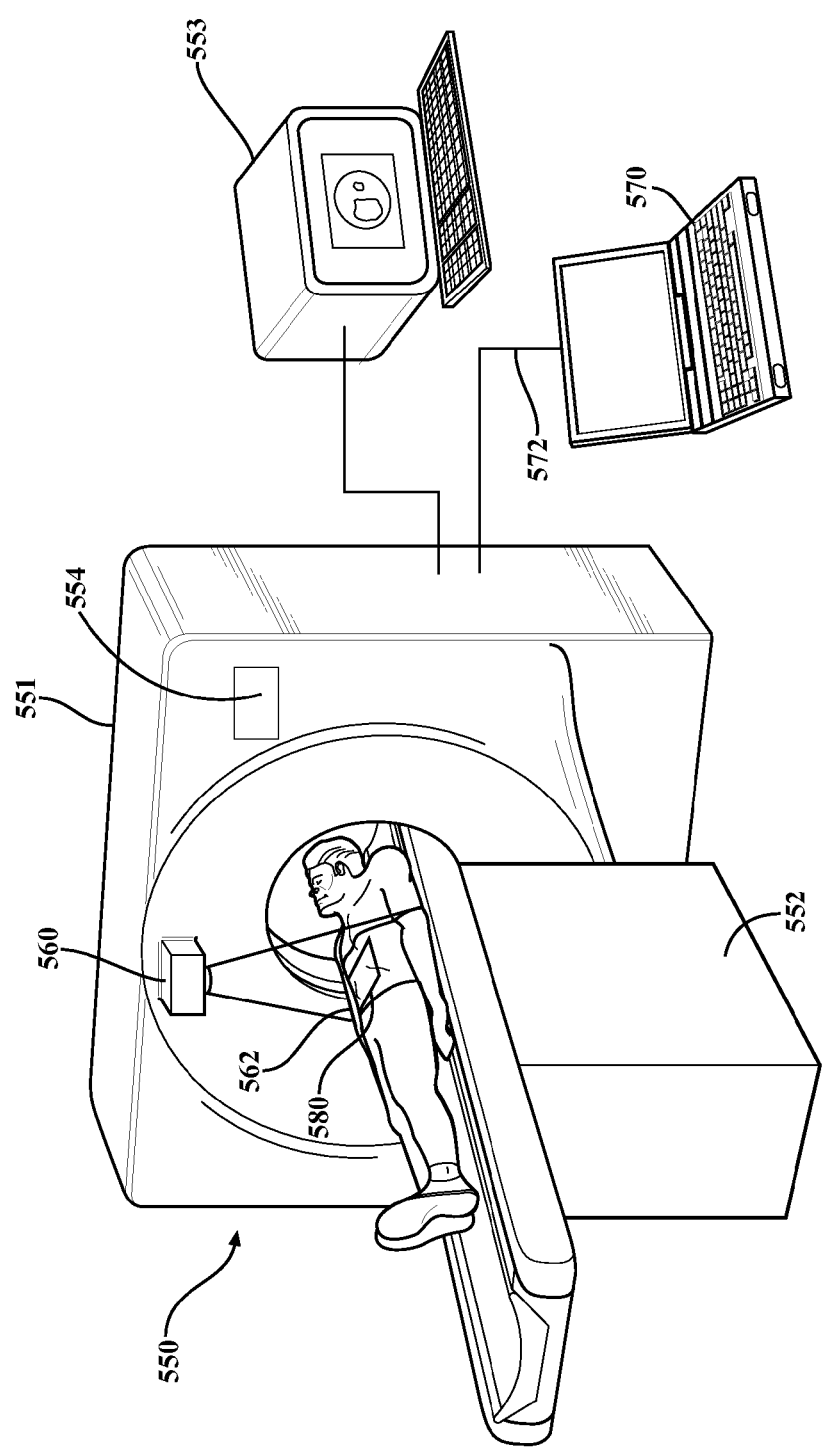
FIG. 4 is a schematic system diagram of a system according to an embodiment of the invention for implementing the method of FIG. 1.
Figure 5:
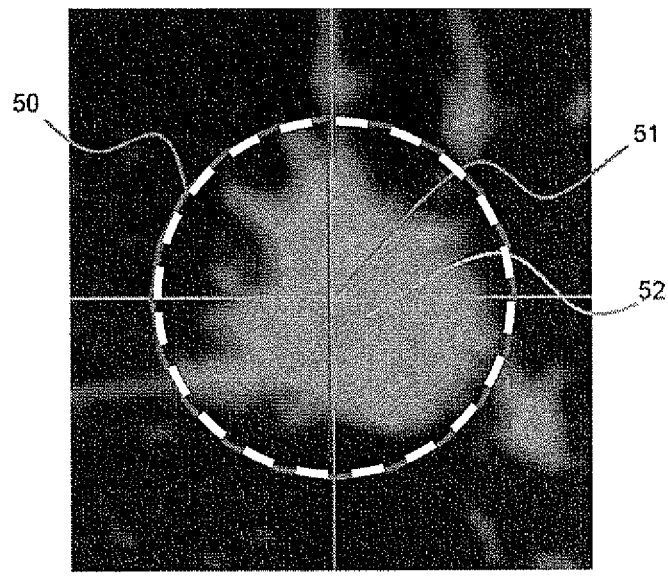
FIGS. 5 and 6 are images generated according to the method of FIG. 1 illustrating effective treatment volumes in the context of CT slice images for a single and a double needle procedure, respectively.

FIG. 4 illustrates an exemplary system in which context the method described above may be implemented, corresponding to a system 550 according to an embodiment of the present invention, for planning a volumetric treatment according to a percutaneous needle procedure in which at least one needle is to be inserted from an entry point to an intra-body target within the body of a subject. In the non-limiting case illustrated here, system 550 is implemented as part of a CT system including a scanner 551, a CT bed 552 and a control unit 553. An optical line projector 560 typically projects a line 562 on the body of the patient. The projected line is a projection, on the body of the patient, of the location of the CT slice of which the coordinates are displayed on a display 554. A computer 570 is connected via a connection line 572 to the CT system. Computer 570 is used to plan the route of the needle in the body of the patient. Computer 570 is preferably a personal computer, although other implementations of a processing system also fall within the scope of the present invention. In one preferred embodiment of the invention, connection line 572 is a USB communication line. In another preferred embodiment of the invention, connection line 572 is PACS network. Other types of communication between computers are applicable in this invention as well. In certain cases, computer 570 may be integrated with CT control unit 553. Computer 570 typically contains a processing system including at least one processor, electronic storage to hold the CT scanned data, a software program for calculating the needle route, a graphic card to calculate and display three dimensional (3D) images and a display to display the resulting images. Optionally, a set of fiducial markers 580, preferably provided in a common frame, may be attached to the patient's skin to assist during the subsequent navigation of the needles, as will be discussed separately below.

The patient is laid on the CT bed. Markers 580 are optionally attached to his or her skin at an estimated neighborhood to the target. If needed, contrast agent is injected to the patient in purpose to enhance the appearance of the lesion and blood vessels in the CT images. A scan is performed, and the resulted images are fed to computer 570, corresponding to step 502 described above. The processing system of computer 570 is configured, typically by suitable software modules operating under a suitable operating system, and with user inputs and display, to perform steps 504-512 as further described above.

Figure 6:
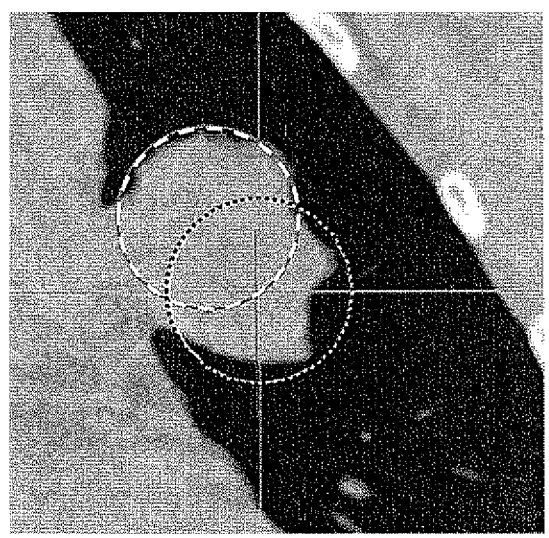

Turning now to FIGS. 5-15, the significance of the system and method described above will be better understood by reference to a number of examples based on actual 3D image data. These examples relate to thermal ablation, in which the distal portion of the needle radiates (or absorbs) heat and creates an ablation zone. It is essential to locate the needle so that the ablation zone envelopes the tumor. That sometimes can be achieved only if the needle is placed at an offset away from the apparent center of the tumor. In the example shown in FIG. 5, the center of the desired ablation zone 51 (i.e., effective treatment volume) is located at an offset away from the center of the tumor 52 in order to cover tumor 50. Moreover, when placing two or more needles in order to cover larger ablation zones, each of the needles is located at an offset away from the center of the tumor, as is seen in FIG. 6. Referring again to FIG. 5, it should be noted that it would be almost impossible to guide the tip of the needle to point 51 without generating a virtual target as an aiming point displayed to the user according to this embodiment. As is evident from the examples of FIGS. 5 and 6, without knowing where the border of the ablation zone falls within the image, it is very hard to plan the correct location of the targets. It is even more difficult to guide the needle to the target, because there is no definite point such as an anatomical landmark to relate to as a target.

Figure 7:
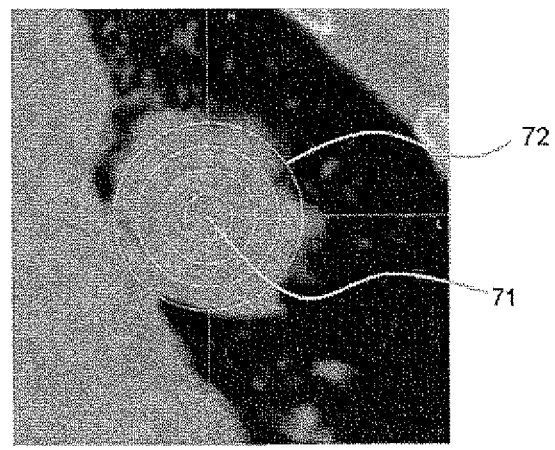
FIGS. 7-15 are a sequence of display images during use of a user-operated implementation of the method of FIG. 2.
Figure 8:
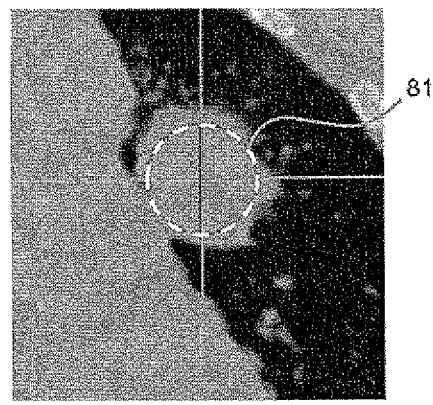
Figure 9:
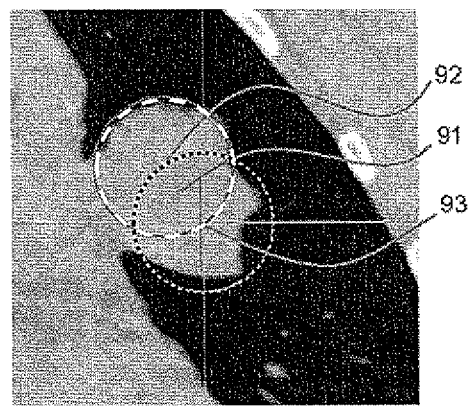
Figure 10:
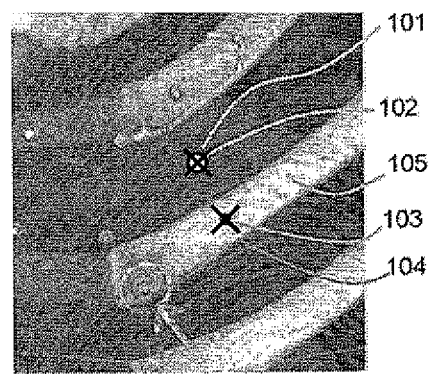
Figure 11:
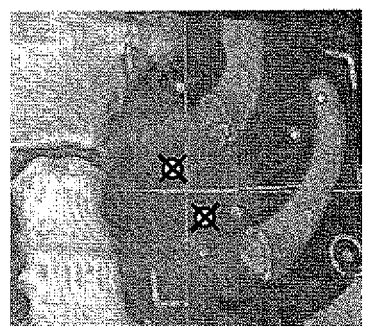
Figure 12:
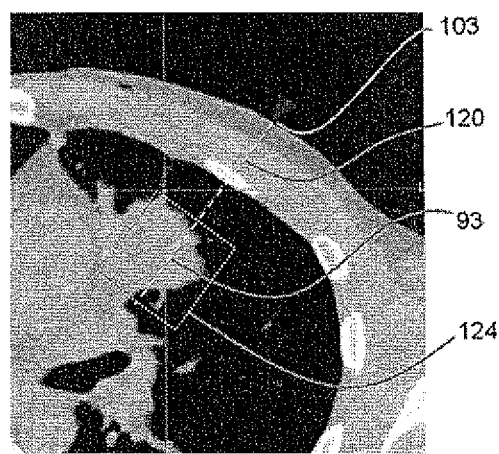
Figure 13:
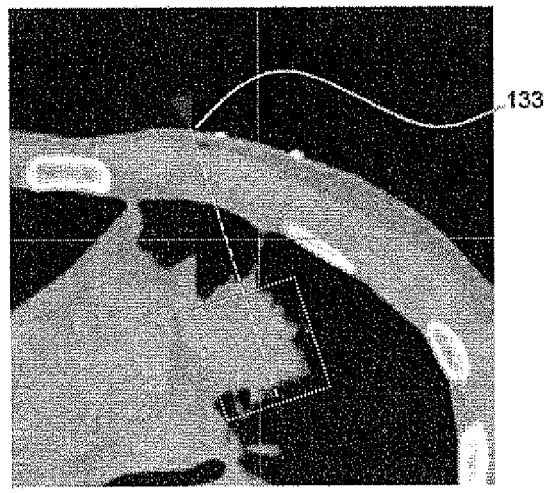
Figure 14:
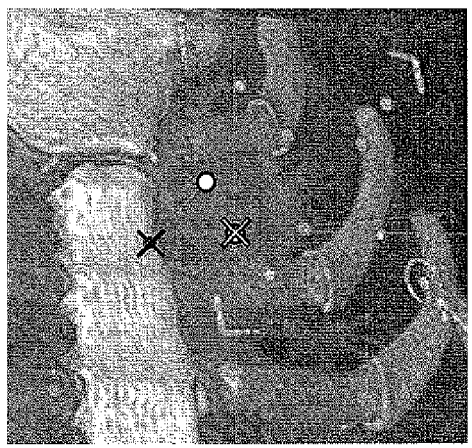
Figure 15:
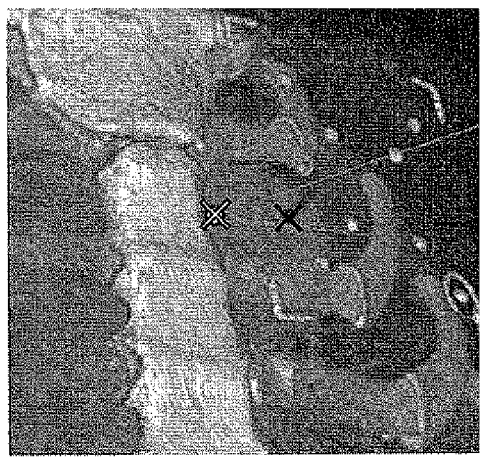

FIGS. 7-15 illustrate graphically a typical non-limiting sequence of operation according to the manual alignment option of FIG. 2. The body portion to be treated is scanned to produce a volume of cross-section images. The images are transferred to the system, preferably in a DICOM format. The tumor should be identified and a center point 71, having equidistance to the border of the tumor, is marked, as seen in FIG. 7. The center point may be located using a special measuring cursor 72 comprised of multiple concentric rings, each having known radius. For instance, the inner ring may have a radius of 10 mm and the radius of each of the following rings may increase by 10 mm. To locate the center point precisely, cross section images of the axial, the sagittal and the coronal views are used in sequence to locate the point until the center is correctly located on all views. After the center point has been selected, the system displays the border of the effective treatment volume, in this case the ablation zone 81, of a single needle, as shown in FIG. 8. If, as shown here, the ablation zone cannot envelope the tumor entirely, more than one needle should be used. When more than one needle is needed, the needle's distance and orientation relative to one another are adjusted to achieve maximum coverage of their combined ablation zones. This can be done manually or predefined according to known parameters of the probe. Referring to FIG. 9, rotation of points 92 and 93 around the center of tumor 91 is possible, until the ablation zones fully envelope the tumor. Referring now to FIG. 10, a 3D volume rendering of the body and the target point is performed in order to select unobstructed paths. The ablation points are represented by hollow circles. In FIG. 10, the center of ablation previously identified as 92 is here displayed in the 3D image as circle 101, and in addition, the entry point of the needle as calculated by the intersection of the path and the skin is presented by an "X" 102 for the path to point 92. As for the other path of this example, the path to the center of ablation 93 is blocked by rib 105, so only the entry point 103 is seen while circle 104 is hidden under the rib. In order to find paths clear of obstructions for both needles, the entry points need to be repositioned. The system preferably allows this to be done by either of two techniques. In the first approach, the 3D volume rendering image of the entire body may be rotated around the center of the tumor 71, until all treatment volume circles are visible without obstruction, as is in FIG. 11. In the second technique, a cross-sectional image of the body along the path is displayed. Referring to FIG. 12, the second path 120 displayed as a dashed line, connects the center of ablation 93 to entry point 103. Ablating zone 124 is also displayed. By rotating path 120 around the center of ablation 93, the entry point location is changed to a more suitable location 133, as is seen in FIG. 13. It is also possible to change each of the paths individually by holding the path to be changed so its entry point coincides with its center of ablation, and rotating the other paths together with the entire volume to find a path clear of obstruction. FIGS. 14 and 15 demonstrate individual entry point relocation for the two paths of the example.

Optical Registration

Turning now to a second aspect of the present invention, this relates to a system and method for determining the position of a set of optical navigation markers on the surface of a body.

Figure 16:
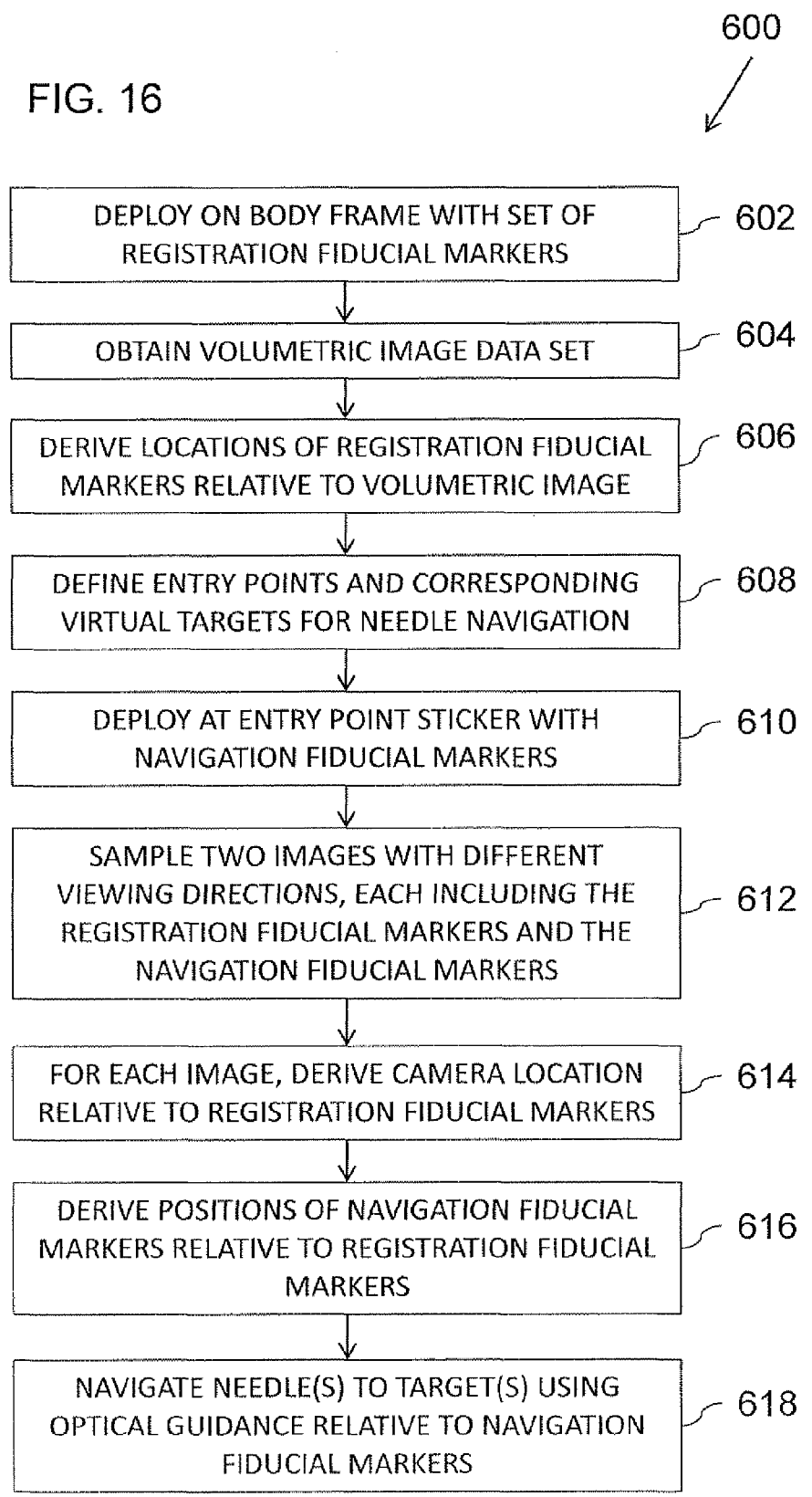
FIG. 16 is a flow diagram of a method according to an embodiment of a further aspect of the present invention for achieving registration of optical markers for use in navigation during a percutaneous needle procedure.

Specifically, referring to FIG. 16, there is shown a method, generally designated 600, according to an embodiment of the present invention, for determining the position of a set of optical navigation markers on the surface of a body. On a conceptual level, this embodiment of the invention allows for optical correlation between a first set of optical fiducial markers and a second set of optical fiducial markers. This in turn allows registration of the second set of markers against other coordinate systems to which the first set of markers are registered, and hence provides a range of advantageous functionality, as will be discussed further below.

Thus, the method includes deploying on the surface of the body a set of at least four registration fiducial markers (step 602). In a particularly preferred but non-limiting set of applications, this first set of markers is registered to a coordinate system of a 3D volume image of the body. According to this option, the first set of markers are positioned prior to obtaining a volumetric image data set (step 604), and locations of the registration fiducial markers are derived relative to the volumetric image (step 606). In a first preferred example, the markers may be implemented as, or combined with, markers which are readily discernable in the image modality of the volumetric imaging system, thereby allowing them to be located directly from the 3D image. Alternatively, registration to the volumetric image may be achieved by an integrated arrangement of optical image sensors combined with the volumetric imaging system, such as will be described below with reference to FIG. 21.

In applications for percutaneous needle procedures, planning of the procedure is preferably performed at this point (step 608) to define entry points and corresponding virtual targets for each needle (or needle position) to be inserted. The planning can be performed by any suitable technique, but is most preferably according to a planning sequence described herein with reference to FIGS. 1-15.

In preparation for performing a procedure, a set of navigation fiducial markers are deployed on the surface of the body, preferably at or near the designated entry point (step 610). Provision of navigation markers at or near the entry point facilitates optical navigation of the needle such as by the techniques disclosed in the aforementioned WO 2007/113815. However, since the entry point was not known prior to performing imaging at step 604 and planning the procedure at step 608, the navigation fiducial markers were not present at the time of the original imaging and are therefore not registered to the volumetric image data. According to the conventional approach, repeated imaging of the body would then be required to achieve registration of the new markers to the volumetric image. Instead, this aspect of the present invention provides a purely optics-based method for transfer-registration from the first set of markers to the second set of markers.

Thus, at step 612, an imaging system including at least one camera is used to obtain at least two optical images taken along different viewing directions, each of the at least two images including both the registration fiducial markers and the navigation fiducial markers. The two images may be sampled using a single camera sequentially in different positions, or two separate cameras. For each image, the positions of the four registration fiducial markers can be used, as will be detailed below, to derive the position and orientation of the camera relative to the registration fiducial markers, and hence also relative to the 3D image data (step 614). Once the camera positions for the two images are resolved, the images can be processed by stereo-visual processing to determine the location of each marker of the navigation fiducial markers relative to the registration fiducial markers and the 3D image data (step 618).

Clearly, once the navigation fiducial markers are registered to the 3D image data, they can be used as discussed previously to facilitate navigation of a needle to an intra-body target defined in the 3D image data coordinate system.

Figure 17:
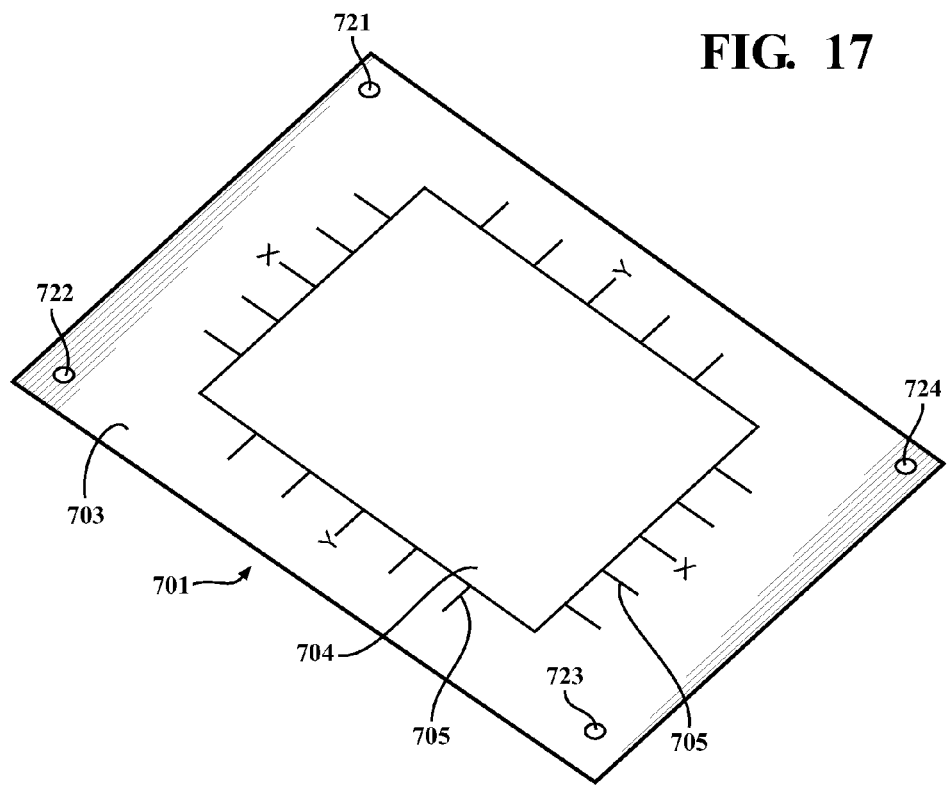
FIG. 17 is a schematic illustration of a frame carrying a set of registration fiducial markers for use in the method of FIG. 16.
Figure 18:
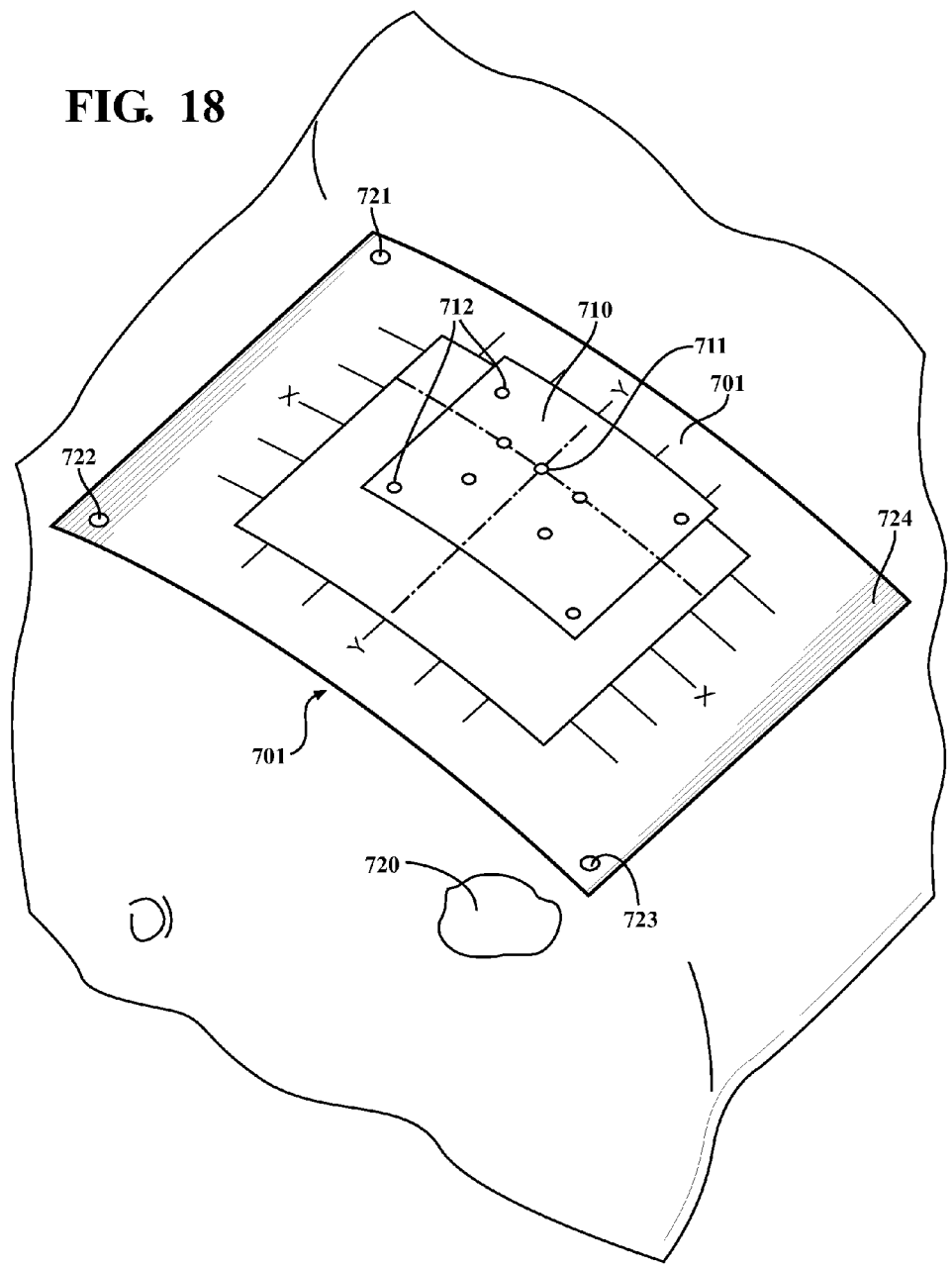
FIG. 18 is a schematic illustration of the frame of FIG. 17 together with a sticker carrying navigation fiducial markers, both applied to a body (not shown) having an intra-body target.
Figure 19:
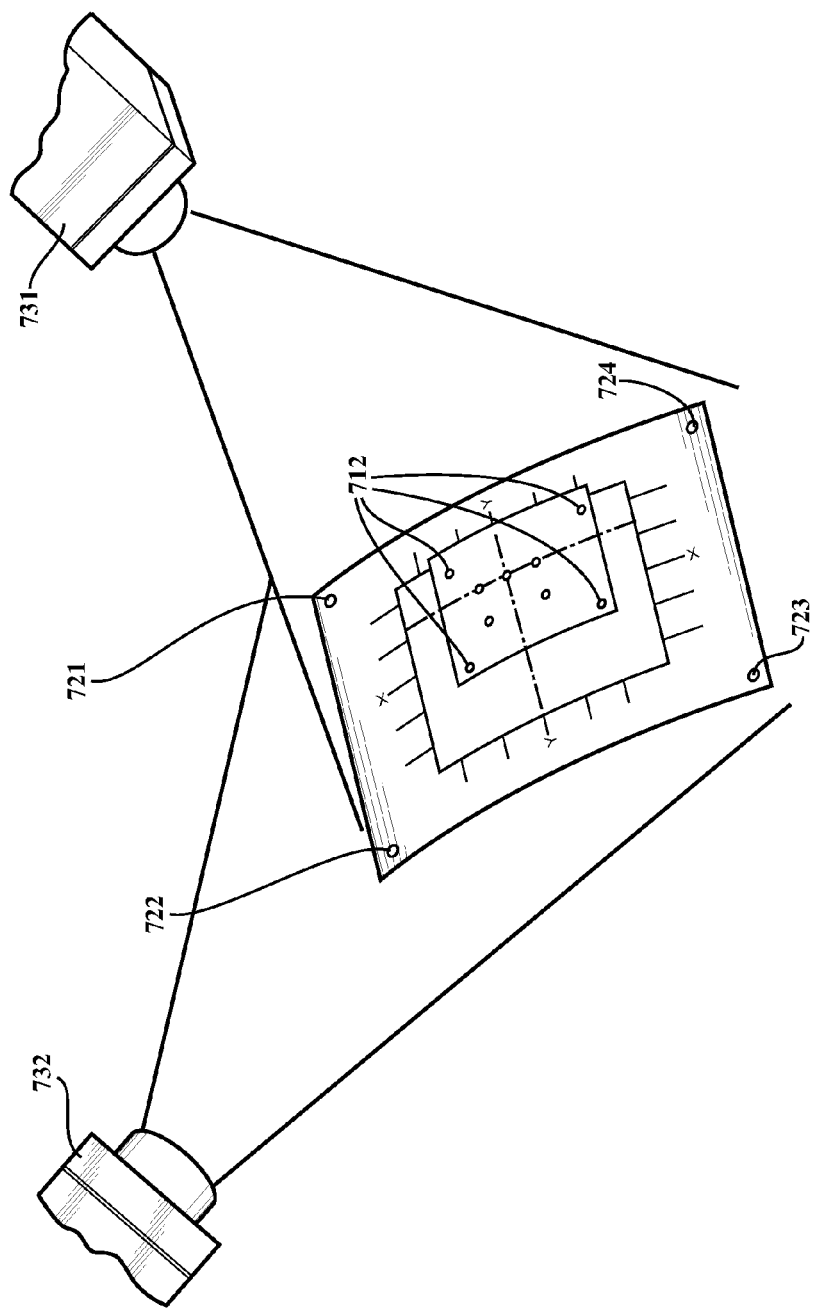
FIG. 19 is a schematic illustration of image sampling steps from the method of FIG. 16.

Turning now to FIGS. 17-19, these illustrate various stages of implementation of the method of FIG. 16, corresponding also to part of a system according to an embodiment of the present invention. Specifically, FIG. 17 shows a sticker 701, constructed as a frame 703 at least partially defining an opening 704. The sticker has at least four fiducial points 721 to 724 embedded in it. Since the sticker is flexible, the location of the fiducials (either mutually or absolutely) may not be known in advance. In a first preferred embodiment of the invention the fiducials are designed to be identifiable by both a video camera and the volumetric imaging modality. As described in WO 2007/113815, by combining color printing with contrast material it is possible to make the fiducial points identifiable unambiguously in the video images and in the 3D images. Explanation of techniques to print such fiducial points on a sticker may be found there, as well as in US patent application publication number US 2009/0290174, which is fully incorporated here by its reference. In addition, a grid of marks 705 is also preferably printed on sticker 701. The sticker can be constructed from thin flexible material and covered with an adhesive layer on the back that makes it easy to attach it to the body. For example, it can be made of a paper, printed on one side and covered with two sided adhesive layer on the other side.

As shown in FIG. 18, sticker 701 is attached to the body with its opening 704 placed over the general area through which the physician wishes to insert the needle. A 3D volumetric scan of the body using an imaging modality appropriate for the clinical indication is performed and the images are used to select the target into which the needle needs to be guided. Based on the 3D volumetric image data, planning software is used to determine the path (or paths) required for the procedure, each path being defined by a skin entry point and the corresponding intra-body target. An example of suitable software is described in WO 2008/107874 and expanded according to the teachings of the first aspect of the present invention, as described above. After the entry point is determined in the coordinate system of the 3D image volume, the software translates these to the 2D coordinates defined by the sticker, preferably corresponding also to a grid 705 printed on its surface. The printed grid may, for example, be a series of lines in the 'x' direction and another, perpendicular to the first, in the 'y' direction, with a spacing of for example 5 mm between the lines. The software also determines from the 3D images the coordinates in space of the fiducial points 702 and the location of the target 720.

After the entry point is determined, the physician prepares the entry location in accordance with the methods defined by the standard of care for performing such procedures, at the location suggested by the software and indicated by the grid on the sticker.

To use the guidance system in accordance with the WO 2007/113815 above, a sticker, which has at least four reference points, is required. These reference points should be seen by the miniature camera that is attached to the needle, as described in WO 2007/113815, along the entire needle path. In order for the camera to see all four reference points even towards the end of its insertion, the reference points (navigation fiducial markers) should be located near the entry point. According to an embodiment of the present invention, the reference points are printed on a second sticker 710, henceforth the Navigation Sticker, which is placed on the skin over the first sticker 701 and/or in opening 704 so as to designate the predetermined entry point. To use the method and the apparatus described in WO 2007/113815, it is necessary to know the coordinates of the reference points used for navigation in the system of coordinates of the image volume. According to WO 2007/113815, it would then be necessary to perform an additional 3D imaging of the navigation sticker to find the positions of the reference points embedded on a sticker (which are in that case combined with contrast material), so their location may be determined from the 3D volume image. According to the preferred aspect of the present invention described here, the coordinates of the reference points on the navigation sticker 710 are determined optically relative to the fiducial points 702 of the grid sticker, without requiring additional 3D imaging or contrast medium in the navigation sticker. The fiducial points of the grid sticker are themselves already known from the prior 3D volume scan, as described above. The physician is thus able to mark an entry point, or multiple entry points for successive insertions, all based on a single initial 3D scan, without requiring repeated scanning each time the navigation sticker is relocated.

FIG. 18 describes an example of the setup required to guide a needle in accordance with the first preferred embodiment of the invention. Navigation sticker 710, having a hole 711 designating the intended insertion point, is attached to the skin over grid sticker 701, at a location defined on grid 705 by two perpendicular 'x' and 'y' coordinates. Sticker 710 has also at least four reference markers 712 used, in accordance with WO 2007/113815, to track the needle.

According to the current invention, the 3D locations of target 720 and fiducial markers 721 to 724 are identified on the image data set. To enable the guidance of the needle to the target, it is necessary to know the 3D locations of markers 712 also. Based on the known coordinates of markers 721-724, this is done by taking two video images of stickers 701 and 710 together from two different directions, and determining the coordinates of fiducial markers 721-724 and reference markers 712 in both images. FIG. 19 shows schematically the required configuration. Based upon the known location $\overline{k}$ of Markers 721-724 in the 3D image, $I_a(k)$ and $I_b(k)$ their corresponding coordinates in the video images of camera a and b respectively, and c the optical transformation constant, the orientations of the cameras, $T_a$ and $T_b$ are determined by solving the following set of linear equations:

$$I_a(\bar{k}) = c \cdot T_a \times \bar{k} \quad (1)$$

$$I_b(\bar{k}) = c \cdot T_b \times \bar{k} \quad (2)$$

For $\bar{r}$, the coordinates of the reference points 712 in the 3D image volume, $\hat{v}_a(\bar{r})$ and $\hat{v}_b(\bar{r})$, their respective coordinates in the video images of camera a and camera b fulfill the following equations:

$$\hat{v}_a(\bar{r}) = c \cdot T_a \times \bar{r} \quad (3)$$

$$\hat{v}_b(\bar{r}) = c \cdot T_b \times \bar{r} \quad (4)$$

Rearranging equation (3) and (4) yields a set of linear equations $$\bar{r} = \frac{1}{c} T_a^{-1} \times \hat{v}_a(\bar{r}) \quad (5)$$

$$\bar{r} = \frac{1}{c} T_b^{-1} \times \hat{v}_b(\bar{r}) \quad (6)$$

The two camera orientations in the two video images ($T_a$, $T_b$) can be calculated from equations (1) and (2) by substituting the known 3D image coordinates ($\bar{k}$) and video coordinates ($I_a(\bar{k})$, $I_b(\bar{k})$) of the fiducial markers 721-724. The coordinates of the reference points ($\bar{r}$) in the space of the 3D imaging modality can then be calculated by solving equations (5) and (6) after substituting the calculated camera orientations ($T_a$, $T_b$) and the video image coordinates of the reference points ($\hat{v}_a(\bar{r})$, vb).

According to one implementation of the first preferred embodiment of this aspect of the invention, a flexible grid sticker 701, having a two dimensional grid of reference coordinates 705 and four identifiable fiducial markers 721-724 printed on its surface, is attached to the body portion of a patient to be treated, a 3D image volume of that body portion including the sticker is taken, the coordinates of said four fiducial markers and a target 720 are determined, the best location of an entry point 711 is determined by two coordinates of the grid on the registration sticker, a navigation sticker 710 having four reference points 712 is attached over the grid sticker, aligned with said two coordinates, two video images from location a and b of the two stickers are taken, and the coordinates of the reference points and the fiducial points in the two video images, are used in conjunction with equations (1)(2) (5) and (6) to determine the coordinates of the reference markers in the 3D image space.

According to another implementation of the first preferred embodiment of the invention, grid sticker 701 comprises plurality of separate registration fiducial markers, each having its own individual sticker, not attached to the others.

Figure 20:
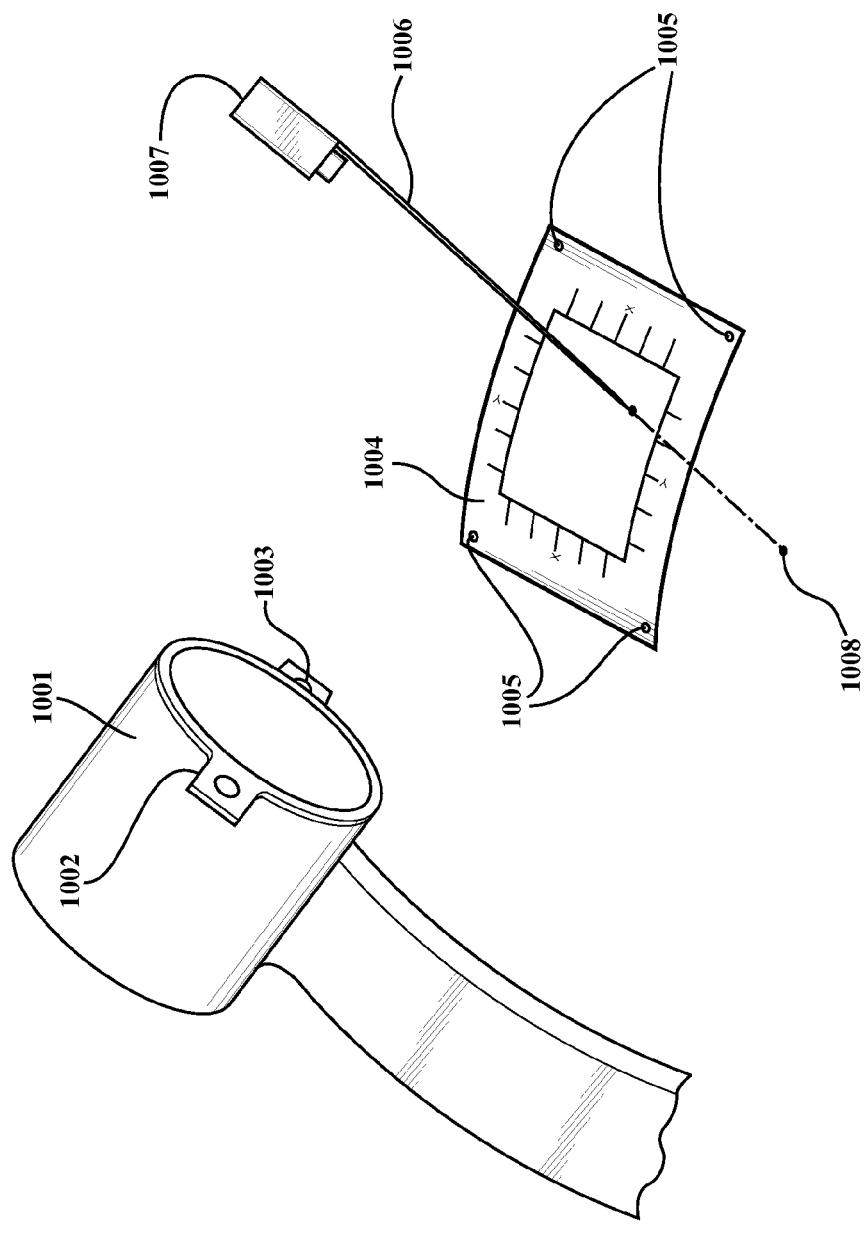
FIG. 20 is a schematic illustration of a modified C-arm fluoroscope according to an embodiment of the present invention.

In a second preferred embodiment of this aspect of the invention, the fiducial markers printed on the grid sticker do not necessarily contain a contrast material and do not need to be identified in the image from the medical imaging device. Instead, in order to determine the required coordinates of the fiducial markers, two video cameras are attached in fixed spatial relation to the imaging device in such a way to cover the location of the grid sticker from two directions. The locations of the fiducial markers are reconstructed from a pair of images taken by those cameras. One example that works in context of a C-arm fluoroscopic imaging device is shown in FIG. 20. A fluoroscope imaging device 1001 is equipped with two video cameras 1002 and 1003. The relative locations of the three imagers (the two video cameras and the fluoroscopy image device) are mutually predetermined as $R_a$ and $R_b$ for the cameras and $R_c$ for the fluoroscope. A grid sticker 1004 is attached to the body of the patient having four optical registration fiducials 1005. Snapshot images are taken by the two video cameras 1002 and 1003 of the grid sticker. The image locations $\hat{v}_a(\bar{r})$ and $\hat{v}_b(\bar{r})$ of the fiducial points 1005 in camera 1002 and 1003 respectfully are determined. For $\bar{r}$, the coordinates of the registration fiducials 1005, $R_a$ and $R_b$, the orientation of camera a and b respectfully, the following equations are fulfilled:

$$\hat{v}_a(\bar{v}) = c \cdot R_a \times \bar{r} \quad (7)$$

$$\hat{v}_b(\bar{r}) = c \cdot R_b \times \bar{r} \quad (8)$$

Rearranging equation (7) and (8) yields a set of linear equations $$\bar{r} = \frac{1}{c} R_a^{-1} \times \hat{v}_a(\bar{r}) \quad (9)$$

$$\bar{r} = \frac{1}{c} R_b^{-1} \times \hat{v}_b(\bar{r}) \quad (10)$$

Solving equations (9) and (10) for the images of fiducials 1005 in the pair snapshots taken by the video cameras 1002 and 1003 yields their coordinates in space.

Once $\bar{r}$ is determined, a tool equipped with a tracking camera 1007 can be guided relative to the fiducials of the grid sticker, or by registering an additional navigation sticker with fiducial markers to the grid sticker fiducials by optical techniques, as described above. Moreover, cameras 1002 and 1003 together with the predetermined orientation $R_c$ can be used to determine the orientation of the fluoroscope relative the grid sticker, and hence to display a projection of the tool on images taken by the fluoroscope.

Figure 21:
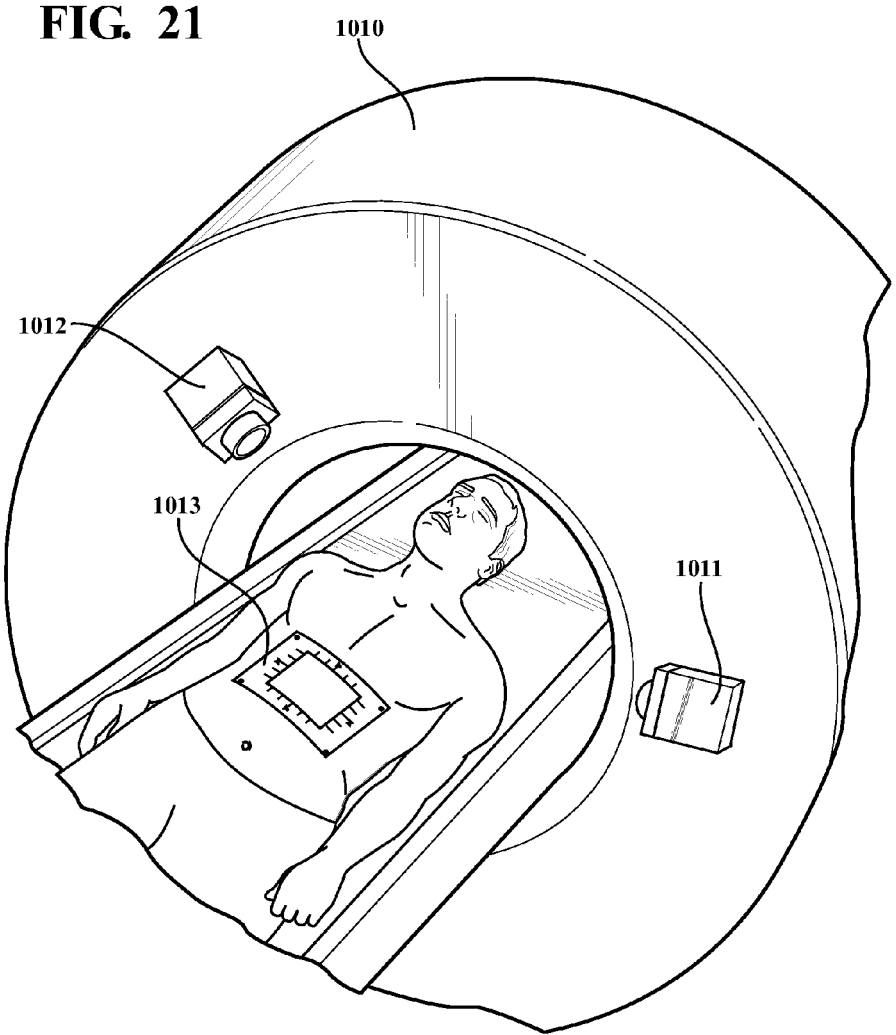
FIG. 21 is a schematic illustration of a modified volume imaging device gantry according to an embodiment of the present invention.

Another implementation of the same principles in the context of a CT imaging device is shown in FIG. 21. Two video cameras 1011 and 1012 are attached in fixed spatial relation to a CT imaging device 1010. The mutual locations of the video cameras and the CT are predetermined. Sticker 1013, having four registration fiducials, is attached to the body of the patient. The CT bed is brought to a known slice location and then a pair of video image snapshots of the sticker are taken, determining the location of the registration fiducials printed on the sticker in the coordinates of the CT. Alternatively, the pair of images are taken synchronously with the start of the scan. Since every CT image slice contains also its slice location as part of the standard DICOM format, the location of the fiducials as determined by the image can be registered to the CT bed (and hence to the DICOM images) by adding that starting slice location. The synchronization itself can be done using a trigger supplied by the CT hardware, or by placing a sensor sensitive to X-ray radiation in the path of the CT beam. A needle equipped with a camera as described above can then be guided relative to these registration fiducials.

Since the same grid sticker which has plurality of fiducial points may work fine in various imaging modalities, attaching such a sticker to a patient's skin and scanning it with more than one modality of image devices allows simple merging between modalities. As an example, additional image data from other sources can be provided during procedures which are normally performed with a fluoroscope. A grid sticker is attached to the patient, who is then scanned by CT or by MRI and the data transformed to DICOM format prior to the procedure performed with the fluoroscope. During the fluoroscope procedure, the tool can then be displayed superimposed on the DICOM images in addition to being displayed superimposed on the fluoroscope images. This provides the practitioner with additional 3D information regarding the internal organs which would not otherwise be available in such procedures.

In addition to bridging between different imaging modalities for display of information, the present invention may provide outputs for directing operation of the imaging systems. For example, where CT data of a patient scanned with a sticker 701 attached to his or her skin at the area of interest for performing the procedure is available prior to performing a procedure under fluoroscopy, the software may determine the recommended position and orientation of the fluoroscope needed to image the body along the needle direction (planned or currently measured) or to image the needle tip and the surrounding tissue and/or the target, and may provide feedback based on the optical sensors to position the fluoroscope correctly relative to the body, even before the fluoroscope radiation is activated. This is expected to reduce greatly the amount of radiation to which the patient and practitioner are exposed. A similar approach may be adopted in cases where real-time CT scanning of a region of the patient's body is performed, employing the optical registration to ensure correct alignment of the CT equipment relative to the patient's body.

It should be noted that the systems of FIGS. 20 and 21 are highly significant in their own right as providing a system and method for achieving registration between an intra-body target and a set of optical fiducial markers without requiring the optical markers to be visible to the volumetric imaging modality. Thus, in general terms, a system according to this aspect of the invention includes a volume imaging device for generating images of the body and two optical image sensors deployed in known spatial relation to the volume imaging device. A processing system, associated with the volume imaging device and the optical image sensors, is configured to process images from the two optical image sensors to derive locations of the optical fiducial markers relative to the optical image sensors, and to define locations of the optical fiducial markers within a coordinate system of the volume imaging device.

In the case of FIG. 20, the volume imaging system is a C-arm fluoroscope 1001, and the two optical image sensors 1002 and 1003 are mounted on the C-arm. In the case of FIG. 21, the volume imaging system is a volumetric imaging system such as a CT system having a gantry 1010, and the two optical image sensors 1011 and 1012 are mounted on the gantry.

This aspect of the present invention also facilitates a range of advantageous methods. For example, particularly in the fluoroscopy implementation of FIG. 20, two fluoroscope images may be obtained with the fluoroscope deployed in at least two different angular positions. Then, by identifying an intra-body target in both of the fluoroscope images, it is possible to derive a spatial relationship between the intra-body target and the optical fiducial markers.

It will be appreciated that the above descriptions are intended only to serve as examples, and that many other embodiments are possible within the scope of the present invention as defined in the appended claims.

What is claimed is:

1. A method for determining the position of a set of optical navigation markers on the surface of a body, the method comprising the steps of:
   (a) deploying on the surface of the body a set of at least four first fiducial markers, wherein the locations of the first fiducial markers relative to each other are known;
   (b) deploying on the surface of the body a set of at least four second fiducial markers, said set of second fiducial markers being distinct from said set of first fiducial markers;
   (c) employing an imaging system including at least one two-dimensional imaging device to obtain at least two images taken along different viewing directions, each of said at least two images including both said first fiducial markers and said second fiducial markers;
   (d) deriving, from positions of said set of first fiducial markers measured from each of said images and from the known locations of the first fiducial markers relative to each other, a corresponding position and orientation of said imaging system relative to said first fiducial markers for each said image; and
   (e) deriving, from positions of said set of second fiducial markers measured from said at least two images and from the corresponding position and orientation of said imaging system for each said image, a position of said second fiducial markers in a frame of reference associated with said first fiducial markers.

2. The method of claim 1, wherein said at least one imaging device is a video camera.

3. The method of claim 1, wherein the first set of fiducial markers comprises a set of registration fiducial markers, and wherein the second set of fiducial markers comprises a set of navigation fiducial markers.

4. The method of claim 3, further comprising the steps of
   (a) obtaining a volumetric image of at least part of the body including a target, subsequent to deploying of said registration fiducial markers and prior to deploying of said navigation fiducial markers;
   (b) deriving locations of said registration fiducial markers relative to said volumetric image; and
   (c) deriving a position of said target relative to said navigation fiducial markers.

5. The method of claim 4, wherein said registration fiducial markers include markers readily discernable in the volumetric image, thereby facilitating said deriving locations of said registration fiducial markers.

6. The method of claim 4, wherein said deriving locations of said registration fiducial markers includes sampling optical images of said registration fiducial markers from two optical image sensors deployed in known spatial relation to a volumetric imaging system employed to obtain said volumetric image.

7. The method of claim 4, further comprising:
   (a) providing a tool having a camera mounted in fixed relation thereto, and deployed so as to obtain images including said navigation fiducial markers; and
   (b) providing a navigation display indicative of a relative position between the tool and the target derived from the position of said navigation fiducial markers within said images.

8. The method of claim 1, comprising deriving the corresponding position and orientation of said imaging system relative to a coordinate system associated with the first fiducial markers.

9. The method of claim 8, comprising deriving the position of said second fiducial markers relative to the coordinate system associated with the first fiducial markers.

10. The method of claim 1, wherein all the second fiducial markers are in different locations than the first fiducial markers.

11. The method of claim 1, wherein the body is the body of a surgical patient.

* * * * *